(12) United States Patent
Giftakis et al.

(10) Patent No.: US 8,000,788 B2
(45) Date of Patent: Aug. 16, 2011

(54) IMPLANTABLE MEDICAL DEVICE FOR TREATING NEUROLOGICAL CONDITIONS INCLUDING ECG SENSING

(75) Inventors: Jonathon E. Giftakis, Maple Grove, MN (US); Nina M. Graves, Minnetonka, MN (US); Jonathan C. Werder, Corcoran, MN (US); Eric J. Panken, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 663 days.

(21) Appl. No.: 11/796,382

(22) Filed: Apr. 27, 2007

(65) Prior Publication Data
US 2008/0269842 A1    Oct. 30, 2008

(51) Int. Cl.
*A61N 1/36* (2006.01)
(52) U.S. Cl. ........... 607/9; 607/1; 607/4; 607/5; 607/15; 607/16; 607/17; 607/18; 607/116; 600/378
(58) Field of Classification Search .......... 607/9, 15–18, 607/116, 4–5, 1; 600/378
See application file for complete search history.

(56) References Cited

U.S. PATENT DOCUMENTS

| | | | |
|---|---|---|---|
| 4,374,382 A | 2/1983 | Markowitz | |
| 4,485,813 A | 12/1984 | Anderson et al. | |
| 4,495,950 A | 1/1985 | Schneider | |
| 4,503,857 A | 3/1985 | Boute et al. | |
| 4,556,063 A | 12/1985 | Thompson et al. | |
| 4,567,892 A | 2/1986 | Plicchi et al. | |
| 4,596,251 A | 6/1986 | Plicchi et al. | |
| 4,702,254 A | 10/1987 | Zabara | |
| 4,862,144 A | 8/1989 | Tao | |
| 4,867,164 A | 9/1989 | Zabara | |
| 4,903,701 A | 2/1990 | Moore et al. | |
| 4,987,897 A | 1/1991 | Funke | |
| 5,003,976 A | 4/1991 | Alt | |
| 5,025,807 A | 6/1991 | Zabara | |
| 5,052,388 A | 10/1991 | Sivula et al. | |
| 5,113,859 A | 5/1992 | Funke | |
| 5,127,404 A | 7/1992 | Wyborny et al. | |
| 5,168,759 A | 12/1992 | Bowman | |

(Continued)

FOREIGN PATENT DOCUMENTS

EP    0512577    11/1992

(Continued)

OTHER PUBLICATIONS

Frei MG, Osorio I. Left vagus nerve stimulation with the neurocybernetic prosthesis has complex effects on heart rate and on its variability in humans. Epilepsia. Aug. 2001;42(8):1007-1016. Presented in part at the American Epilepsy Society Annual Meetings San Francisco, CA, 1996, and San Diego, CA, 1998).

(Continued)

*Primary Examiner* — Carl H Layno
*Assistant Examiner* — Deborah Malamud
(74) *Attorney, Agent, or Firm* — Fredrikson & Byron, PA (57) ABSTRACT

An implantable medical device such as an implantable pulse generator that includes EEG sensing for monitoring and treating neurological conditions, and leadless ECG sensing for monitoring cardiac signals. The device includes a connector block with provisions for cardiac leads which may be used/enabled when needed. If significant co-morbid cardiac events are observed in patients via the leadless ECG monitoring, then cardiac leads may be subsequently connected for therapeutic use.

41 Claims, 5 Drawing Sheets

U.S. PATENT DOCUMENTS

| | | | |
|---|---|---|---|
| 5,203,326 | A | 4/1993 | Collins |
| 5,271,395 | A | 12/1993 | Wahlstrand et al. |
| 5,312,451 | A | 5/1994 | Limousin et al. |
| 5,314,430 | A | 5/1994 | Bardy |
| 5,336,244 | A | 8/1994 | Weijand |
| 5,354,316 | A | 10/1994 | Keimel |
| 5,354,318 | A | 10/1994 | Taepke |
| 5,409,009 | A | 4/1995 | Olson |
| 5,509,927 | A | 4/1996 | Epstein et al. |
| 5,545,186 | A | 8/1996 | Olson et al. |
| 5,554,177 | A | 9/1996 | Kieval et al. |
| 5,560,368 | A | 10/1996 | Berger |
| 5,562,711 | A | 10/1996 | Yerich et al. |
| 5,626,622 | A | 5/1997 | Cooper |
| 5,645,068 | A | 7/1997 | Mezack et al. |
| 5,683,432 | A | 11/1997 | Goedeke et al. |
| 5,684,460 | A | 11/1997 | Scanlon |
| 5,713,923 | A | 2/1998 | Ward et al. |
| 5,749,900 | A | 5/1998 | Schroeppel et al. |
| 5,752,976 | A | 5/1998 | Duffin et al. |
| 5,782,891 | A | 7/1998 | Hassler et al. |
| 5,836,988 | A | 11/1998 | Cooper et al. |
| 5,871,517 | A | 2/1999 | Abrams |
| 5,928,272 | A | 7/1999 | Adkins et al. |
| 5,987,352 | A | 11/1999 | Klein et al. |
| 5,995,868 | A | 11/1999 | Dorfmeister et al. |
| 6,029,087 | A | 2/2000 | Wohlgemuth |
| 6,035,233 | A | 3/2000 | Schroeppel et al. |
| 6,067,473 | A | 5/2000 | Greeninger et al. |
| 6,083,248 | A | 7/2000 | Thompson |
| 6,115,630 | A | 9/2000 | Stadler et al. |
| 6,128,526 | A | 10/2000 | Stadler et al. |
| 6,134,474 | A | 10/2000 | Fischell et al. |
| 6,155,267 | A | 12/2000 | Nelson |
| 6,185,459 | B1 | 2/2001 | Mehra et al. |
| 6,200,265 | B1 | 3/2001 | Walsh et al. |
| 6,263,237 | B1 | 7/2001 | Rise |
| 6,280,461 | B1 | 8/2001 | Glegyak et al. |
| 6,337,997 | B1 | 1/2002 | Rise |
| 6,341,236 | B1 | 1/2002 | Osorio et al. |
| 6,353,754 | B1 | 3/2002 | Fischell et al. |
| 6,360,122 | B1 | 3/2002 | Fischell et al. |
| 6,363,274 | B1 | 3/2002 | Scalisi et al. |
| 6,366,813 | B1 | 4/2002 | DiLorenzo |
| 6,415,174 | B1 | 7/2002 | Bebehani et al. |
| 6,427,086 | B1 | 7/2002 | Fischell et al. |
| 6,463,328 | B1 | 10/2002 | John |
| 6,466,822 | B1 | 10/2002 | Pless |
| 6,473,639 | B1 | 10/2002 | Fischell et al. |
| 6,480,743 | B1 | 11/2002 | Kirkpatrick et al. |
| 6,496,175 | B1 | 12/2002 | Fukuo |
| 6,496,715 | B1 | 12/2002 | Lee et al. |
| 6,505,067 | B1 | 1/2003 | Lee et al. |
| 6,512,940 | B1 | 1/2003 | Brabec et al. |
| 6,512,949 | B1 | 1/2003 | Combs et al. |
| 6,522,915 | B1 | 2/2003 | Ceballos et al. |
| 6,549,804 | B1 | 4/2003 | Osorio et al. |
| 6,556,859 | B1 | 4/2003 | Wohlgemuth et al. |
| 6,572,542 | B1 | 6/2003 | Houben et al. |
| 6,587,727 | B2 | 7/2003 | Osorio et al. |
| 6,622,036 | B1 | 9/2003 | Suffin |
| 6,647,292 | B1 | 11/2003 | Bardy et al. |
| 6,650,938 | B1 | 11/2003 | Boute |
| 6,671,555 | B2 | 12/2003 | Gielen et al. |
| 6,671,556 | B2 | 12/2003 | Osorio et al. |
| 6,721,599 | B2 | 4/2004 | De Vries |
| 6,745,076 | B2 | 6/2004 | Wohlgemuth et al. |
| 6,920,357 | B2 | 7/2005 | Osorio et al. |
| 6,934,580 | B1 | 8/2005 | Osorio et al. |
| 6,961,618 | B2 | 11/2005 | Osorio et al. |
| 7,146,218 | B2 | 12/2006 | Esteller et al. |
| 7,162,304 | B1 | 1/2007 | Bradley |
| 7,174,206 | B2 | 2/2007 | Frei et al. |
| 7,177,674 | B2 | 2/2007 | Echauz et al. |
| 7,207,948 | B2 | 4/2007 | Coyle |
| 7,242,983 | B2 | 7/2007 | Frei et al. |
| 7,324,845 | B2 | 1/2008 | Mietus et al. |
| 2002/0072778 | A1* | 6/2002 | Guck et al. ............... 607/36 |
| 2002/0072782 | A1* | 6/2002 | Osorio et al. ............ 607/45 |
| 2002/0099412 | A1 | 7/2002 | Fischell et al. |
| 2002/0107553 | A1 | 8/2002 | Hill et al. |
| 2002/0169485 | A1 | 11/2002 | Pless et al. |
| 2003/0004548 | A1* | 1/2003 | Warkentin ................ 607/9 |
| 2003/0073917 | A1 | 4/2003 | Echauz et al. |
| 2003/0083716 | A1 | 5/2003 | Nicolelis |
| 2003/0149457 | A1 | 8/2003 | Tcheng et al. |
| 2003/0195574 | A1 | 10/2003 | Osorio et al. |
| 2003/0195588 | A1 | 10/2003 | Fischell et al. |
| 2003/0236474 | A1 | 12/2003 | Singh |
| 2004/0006264 | A1 | 1/2004 | Mojarradi et al. |
| 2004/0102816 | A1* | 5/2004 | Mazar et al. ............ 607/27 |
| 2004/0133119 | A1 | 7/2004 | Osorio et al. |
| 2004/0133120 | A1 | 7/2004 | Frei et al. |
| 2004/0133248 | A1 | 7/2004 | Frei et al. |
| 2004/0133390 | A1 | 7/2004 | Osorio et al. |
| 2004/0138516 | A1 | 7/2004 | Osorio et al. |
| 2004/0138517 | A1 | 7/2004 | Osorio et al. |
| 2004/0138518 | A1 | 7/2004 | Rise et al. |
| 2004/0138536 | A1 | 7/2004 | Frei et al. |
| 2004/0138580 | A1 | 7/2004 | Frei et al. |
| 2004/0138581 | A1 | 7/2004 | Frei et al. |
| 2004/0138647 | A1 | 7/2004 | Osorio et al. |
| 2004/0138711 | A1 | 7/2004 | Osorio et al. |
| 2004/0138721 | A1 | 7/2004 | Osorio et al. |
| 2004/0152958 | A1 | 8/2004 | Frei et al. |
| 2004/0158119 | A1 | 8/2004 | Osorio et al. |
| 2004/0176817 | A1 | 9/2004 | Wahlstrand et al. |
| 2004/0181263 | A1 | 9/2004 | Balzer et al. |
| 2004/0199482 | A1 | 10/2004 | Wilson |
| 2004/0215240 | A1* | 10/2004 | Lovett et al. ............. 607/4 |
| 2004/0230105 | A1 | 11/2004 | Geva et al. |
| 2004/0267152 | A1 | 12/2004 | Pineda |
| 2005/0010265 | A1 | 1/2005 | Baru Fassio et al. |
| 2005/0081847 | A1* | 4/2005 | Lee et al. ............ 128/200.24 |
| 2005/0115561 | A1 | 6/2005 | Stahmann et al. |
| 2005/0197590 | A1 | 9/2005 | Osorio et al. |
| 2005/0216071 | A1 | 9/2005 | Devlin et al. |
| 2006/0058856 | A1 | 3/2006 | Morell |
| 2006/0094970 | A1 | 5/2006 | Drew |
| 2006/0094972 | A1 | 5/2006 | Drew |
| 2006/0135877 | A1 | 6/2006 | Giftakis et al. |
| 2006/0135881 | A1 | 6/2006 | Giftakis et al. |
| 2006/0136006 | A1 | 6/2006 | Giftakis et al. |
| 2006/0195144 | A1 | 8/2006 | Giftakis et al. |
| 2006/0206159 | A1 | 9/2006 | Moffitt et al. |
| 2006/0224067 | A1 | 10/2006 | Giftakis et al. |
| 2006/0241725 | A1 | 10/2006 | Libbus et al. |
| 2007/0100392 | A1* | 5/2007 | Maschino et al. ....... 607/45 |
| 2007/0161919 | A1 | 7/2007 | DiLorenzo |
| 2007/0238939 | A1 | 10/2007 | Giftakis |
| 2007/0239054 | A1 | 10/2007 | Giftakis |
| 2007/0239060 | A1 | 10/2007 | Giftakis |
| 2007/0239230 | A1 | 10/2007 | Giftakis |
| 2007/0260147 | A1 | 11/2007 | Giftakis |
| 2007/0260286 | A1 | 11/2007 | Giftakis |
| 2007/0260289 | A1 | 11/2007 | Giftakis |
| 2007/0265536 | A1 | 11/2007 | Giftakis |
| 2007/0265677 | A1 | 11/2007 | Giftakis |
| 2008/0033490 | A1 | 2/2008 | Giftakis |

FOREIGN PATENT DOCUMENTS

| | | |
|---|---|---|
| WO | 02/34332 | 5/2002 |
| WO | 0234332 A1 | 5/2002 |
| WO | WO 02/36003 | 5/2002 |
| WO | WO 02/49500 | 6/2002 |
| WO | 2004/091720 | 10/2004 |
| WO | 2004091720 A2 | 10/2004 |
| WO | WO 9726823 | 8/2008 |

OTHER PUBLICATIONS

Sunderam S, Osorio I, Frei MG, Watkins III JF. Stochastic modeling and prediction of experimental seizures in sprague-dawley rats. J Clin Neurophysiol. May 2001;18(3):275-282.

Osorio I, Harrison MAF, Frei MG, Lai YC. Observations on the application of the correlation dimension and correlation integral to the prediction of seizures. J Clin Neurophysiol. May 2001;18(3);269-274.

Ingram J, Sunderam S, Frei MG, Osorio, I. Autonomic regulation during complex partial seizures: A thermographic study. Abstract; Epilepsia. 41(S7);59. Proceedings of the 54th Annual Meeting of the American Epilepsy Society, Los Angeles, CA, Dec. 1-6, 2000.

Sunderam S, Watkins III JF, Frei MG, and Osorio I. A stochastic analysis of ictal-interictal transitions during experimental seizures: Seizure duration depends on the duration of preceding ictal and interictal states. Abstract; Epilepsia. 41(S7);49. Proceedings of the 54th Annual Meeting of the American Epilepsy Society, Los Angeles, CA, Dec. 1-6, 2000.

DiTeresi CA, Thompson M, Frei MG, Sunderam S, and Osorio I. Loss of function during partial seizures: A quantitative study in humans. Abstract; Epilepsia. 41(S7);237. Proceedings of the 54th Annual Meeting of the American Epilepsy Society, Los Angeles, CA, Dec. 1-6, 2000.

Nagaraddi V, Wilkinson SB, Osorio I. The effect of one hertz stimulation on kindled seizures in rats. Abstract; Proceeding of the 54th Annual Meeting of the American Epilepsy Society, Los Angeles, CA, Dec. 1-6, 2000.

Frei MG, Davidchack R, Osorio I. Least squares acceleration filtering for estimating signal derivatives and Sharpness at extrema. IEEE. Aug. 1999; 46(8):971-977.

Osorio I, Frei MG, Wilkinson SB. Real time automated detection and quantitative analysis of seizures and short term predictions of clinical onset. Epilepsia. 1998;39(S16):615-627.

Thomas CV, Angel CA, Watkins JM, Frei MG, Bunag RD, Osorio I. Effects of vagal and sciatic stimulation on 3-MPA-induced seizures in rats. Epilepsia. 1998;39(S6):29.

Frei MG, Haas SM, Ingram JL, Osorio I. Filter design methods for improved seizure detection. Epilepsia. 1998;39 (S6):108.

Powell J, Frei MG, Davidchak R, Watkins JM, Wilkinson SB, Osorio I. Ictal tachycardia does not closely correlate with electrographic onset of ictal ECoG frequency changes. Epilepsia. 1998;39(S6):112.

Frei MG, Davidchack R, Osorio I. Effects of vagal stimulation on human ECG. Epilepsia. 1998:39(S6):200.

Frei MG, Osorio I, Davidchack R. A reappraisal of the value of EKG in the detection of epileptic seizures. Abstract; Epilepsia. 1996:37(S5). Poster presentation, 50th Annual Meeting of the American Epilepsy Society, San Francisco, CA., Dec. 8, 1996.

Han P, Frei MG, Osorio I. Probable mechanisms of action of vagus nerve stimulation in humans with epilepsy: Is the heart a window into the brain? Abstract; Epilepsia. 1996:37(S5):83. Platform presentation, 50th Annual Meeting of the American Epilepsy Society, San Francisco, CA, Dec. 8, 1996.

Frei MG, Osorio I, Wilkinson SB. Quantitative analysis of inter-ictal vs. ictal ECoG signals. Abstract; Epilepsia. 1995:36 (S4):5. Poster presentation, 49th Annual Meeting of the American Epilepsy Society, Baltimore, MD, Dec. 4, 1995.

Osorio I, Frei MG, Lerner D, Wilkinson S. A method for accurate automated real time seizure detection. Abstract; Epilepsia. 1995:36(S4):4. Poster presentation, 49th Annual Meeting of the American Epilepsy Society, Baltimore, MD, Dec. 4, 1995.

Ingram J, Osorio I, Frei MG, Wilkinson SB, Troster A. Temporo-spatial behavior of seizures of temporal lobe origin. Abstract; Epilepsia. 1995:36(S4):9. Poster presentation, 49th Annual Meeting of the American Epilepsy Society, Baltimore, MD, Dec. 4, 1995.

Hayden R, Lerner D, Osorio I, Lai YC, Frei MG.Correlation dimension does not distinguish ictal from interictal activity or noise. Abstract; Epilepsia. 1995:36(S4):5. Poster presentation, 49th Annual Meeting of the American Epilepsy Society, Baltimore, MD, Dec. 4, 1995.

Osorio I, Frei MG, Lerner D, Wilkinson SB. Automated rapid seizure detection in the human ECoG. Abstract in Proceedings of the IEEE Computer-Based Medical Systems, Lubbock, TX, Jun. 9-12, 1995.

Blum M, Floyd R, Vaughan P, Rivest R, Tarjan R. Linear Time Bounds for Median Computations. Abstract in *, Aug. 1971.

Hastad J. Median finding. Advanced Algorithms. Lecture 11: May 3, 1995.

Leutmezer, et al., "Electrocardiographic Changes at Seizure Onset," Epilepsia, 2003, pp. 348-354, 44(3).

Rocamora, et al., "Cardiac Asystole in Epilepsy: Clinical and Neurophysiologic Features," Epilepsia, 2003, pp. 179-185, 44(2).

Tavernor, et al., "Electrocardiograph QT Lengthening Associated with Epileptiform EEG Discharges—A Role in Sudden Unexplained Death in Epilepsy," Seizure, Mar. 1996, pp. 79-83, 5(1).

Devinsky, "Effects of Seizures on Autonomic and Cardiovascular Function," Epilepsy Currents, Mar./Apr. 2004, pp. 43-46, 4(2).

Donner, et al., "Sudden Unexplained Death in Children with Epilepsy," Neurology, 2001, pp. 430-434, 57.

Nei, et al., "EEG and ECG in Sudden Unexplained Death in Epilepsy," Epilepsia, 2004, pp. 338-345, 45(4).

Notification of Transmittal of the International Search and the Written Opinion, dated Jan. 7, 2008 for corresponding PCT Application No. PCT/US2007/067625 (15 pages).

Vaughn, et al., "Monitoring Heart Period Variability changes During Seizures. II. Diversity and Trends", J. Epilepsy, 1996, p. 27-34, vol. 9.

Pacemaker Stops Epilepsy Deaths, Dec. 2004, BBC News World Edition.

Jones, et al., Heart Rate Responses to Selective Stimulation of Cardiac Vagal C Fibres in Anaesthetized Cats, Rats and Rabbits, 1995, pp. 203-214, J. Physiol. 489.1, London.

Asconape et al., Early Experience with Vagus Nerve Stimulation for the Treatment of Epilepsy: Cardiac Complications, No. 6.058—Abstract from American Epilepsy Society, Epilepsia, 1998, vol. 39, Supp. 6.

Kamath, et al., Neurocardiac responses to Vagoaferent Electrostimulation in Humans, 1992, pp. 1581-1687, PACE, vol. 15.

U.S. Appl. No. 10/997,540, filed Nov. 24, 2004 entitled "A Method and System for Logging Quantitative Seizure Information and Assessing Efficacy of Therapy Using Cardiac Signals".

International Search and the Written Opinion, dated May 3, 2006 for PCT Application No. PCT/US2005/045656 8 pages).

International Search and the Written Opinion, dated May 3, 2006 for PCT Application No. PCT/US2005/045648 8 pages).

International Search and the Written Opinion, dated May 8, 2006 for PCT Application No. PCT/US2005/047628 7 pages).

International Search and the Written Opinion, dated May 8, 2006 for PCT Application No. PCT/US2005/045902 8 pages).

International Search and the Written Opinion, dated May 8, 2006 for PCT Application No. PCT/US2007/067625 13 pages).

U.S. Appl. No. 11/311,200 Notice of Allowance mailed Dec. 5, 2009, 3 pgs.

U.S. Appl. No. 11/311,043 Notice of Allowance mailed Dec. 21, 2009, 1 pgs.

U.S. Appl. No. 11/796,576 Office Action mailed Jan. 8, 2010, 7 pgs.

U.S. Appl. No. 11/796,575 Office Action mailed Mar. 12, 2010, 8 pgs.

U.S. Appl. No. 11/796,577 Office Action mailed Mar. 9, 2010, 8 pgs.

U.S. Appl. No. 11/380,462 Office Action mailed Mar. 15, 2010, 12 pgs.

U.S. Appl. No. 11/311,043 Non Final Office Action mailed Dec. 23, 2008, 8 pgs.

U.S. Appl. No. 11/380,462 Non Final Office Action mailed Apr. 8, 2009, 13 pgs.

U.S. Appl. No. 11/796,576 Non Final Office Action mailed Jun. 17, 2009, 8 pgs.

U.S. Appl. No. 11/311,043 Notice of Allowance mailed Aug. 10, 2009, 4 pgs.

U.S. Appl. No. 11/311,200 Non Final Office Action mailed Aug. 25, 2009, 7 pgs.

U.S. Appl. No. 11/380,462 Final Office Action mailed Nov. 9, 2009, 12 pgs.

International Preliminary Report on Patentability, dated Oct. 27, 2009 for PCT Application No. PCT/US2007/067625 8 pages).

U.S. Appl. No. 11/311,043 Notice of Allowance mailed May 5, 2010, 4 pgs.

U.S. Appl. No. 11/311,200 Notice of Allowance mailed Apr. 20, 2010, 1 pgs.

U.S. Appl. No. 11/311,456 Office Action mailed May 28, 2010, 11 pages.

U.S. Appl. No. 11/311,393 Office Action mailed Jun. 4, 2010, 10 pages.
U.S. Appl. No. 11/311,200 Office Communication mailed Jul. 26, 2010, 6 pgs.
U.S. Appl. No. 11/796,576 Office Action mailed Aug. 20, 2010, 7 pgs.
U.S. Appl. No. 11/796,575 Office Action mailed Aug. 31, 2010, 10 pgs.
U.S. Appl. No. 11/741,103 Office Action mailed Aug. 31, 2010, 11 pgs.
U.S. Appl. No. 11/766,886 Office Action mailed Aug. 31, 2010, 11 pgs.
U.S. Appl. No. 11/741,109 Office Action mailed Sep. 29, 2010, 10 pgs.
U.S. Appl. No. 11/311,393 Notice of Allowance mailed Oct. 1, 2010, 3 pgs.
U.S. Appl. No. 11/380,462 Final Office Action mailed Nov. 1, 2010, 13 pgs.
U.S. Appl. No. 11/311,456 Notice of Allowance mailed Oct. 20, 2010, 1 page.
U.S. Appl. No. 11/311,043 Notice of Allowance mailed Oct. 19, 2010, 4 pages.
U.S. Appl. No. 11/311,200 Notice of Allowance mailed Oct. 12, 2010, 4 pages.
U.S. Appl. No. 11/796,577 Final Office Action mailed Nov. 15, 2010, 9 pgs.
U.S. Appl. No. 11/796,575 Final Office Action mailed Mar. 18, 2011, 11 pages.
U.S. Appl. No. 11/741,119 Office Action mailed Mar. 28, 2011, 28 pages.
U.S. Appl. No. 11/796,576 Final Office Action mailed Mar. 30, 2011, 10 pages.
U.S. Appl. No. 11/766,886 Office Action mailed Apr. 11, 2011, 10 pgs.
U.S. Appl. No. 11/741,109 Final Office Action mailed Apr. 12, 2011, 8 pgs.
U.S. Appl. No. 11/380,462 Office Action mailed Apr. 13, 2011, 7 pgs.
U.S. Appl. No. 11/741,103 Office Action mailed Apr. 13, 2011, 10 pgs.
U.S. Appl. No. 11/796,577 Notice of Allowance mailed May 5, 2011, 13 pgs.

\* cited by examiner

IMPLANTABLE MEDICAL DEVICE FOR TREATING NEUROLOGICAL CONDITIONS INCLUDING ECG SENSING

FIELD

The embodiments of the present invention relate generally to medical devices, and, more particularly, to an implantable device that uses leadless electrodes for sensing cardiac signals and using those sensed signals to determine whether cardiac leads need to be coupled to the implantable device and positioned in or near a patient's heart.

BACKGROUND

Nervous disorders affect millions of people, causing death and a degradation of life. Nervous system disorders include disorders of the central nervous system, peripheral nervous system, and mental health and psychiatric disorders. Such disorders include, for example, without limitation, epilepsy, Parkinson's disease, essential tremor, dystonia, and multiple sclerosis (MS).

Additionally, nervous system disorders include mental health disorders and psychiatric disorders which also affect millions of individuals and include, but are not limited to, anxiety (such as general anxiety disorder, panic disorder, phobias, post traumatic stress disorder (PTSD), and obsessive compulsive disorder (OCD), mood disorders (such as major depression, bipolar depression, and dysthymic disorder), sleep disorders (narcolepsy), eating disorders such as obesity, and anorexia. As an example, epilepsy is the most prevalent serious neurological disease across all ages. Epilepsy is a group of neurological conditions in which a person has or is predisposed to recurrent seizures. A seizure is a clinical manifestation resulting from excessive hypersynchronous, abnormal electrical or neuronal activity in the brain. A neurological event is an activity that is indicative of a nervous system disorder. A seizure is a type of neurological event. This electrical excitability of the brain may be likened to an intermittent electrical overload that manifests with sudden, recurrent and transient changes of mental function, sensations, perceptions, or involuntary body movement. Because the seizures are unpredictable, epilepsy affects a person's employability, psychosocial life, and ability to operate vehicles or power equipment. It is a disorder that occurs in all age groups, socioeconomic classes, cultures, and countries.

Nervous system disorders are often associated with co-morbid life-threatening conditions, which in some cases may have a cardiac cause. For example, a subset of epilepsy patients are at risk for SUDEP. SUDEP is defined as sudden, unexpected, often unwitnessed, non-traumatic and non-drowning death in patients for which no cause has been found except for the individual having a history of seizures. Depending on the cohort studied, SUDEP is responsible for 2% to 18% of all deaths in patients with epilepsy, and the incidence may be up to 40 times higher in young adults with epilepsy than among persons without seizures.

Although the pathophysiological mechanisms leading to death are not fully understood, experimental, autopsy and clinical evidence implicate seizure related heart and pulmonary dysfunction or indicators. Pulmonary events may include obstructive sleep apnea (OSA), central apnea, and neurogenic pulmonary edema. Cardiac events may include cardiac arrhythmic abnormalities including sinus arrhythmia, sinus pause, premature atrial contraction (PAC), premature ventricular contraction (PVC), irregular rhythm (wandering pacemaker, multifocal atrial tachycardia, atrial fibrillation), asystole or paroxysmal tachycardia. Cardiac events may also include conduction abnormalities including AV-block (AVB) and bundle branch block (BBB) and repolarization abnormalities including T-wave inversion and ST-elevation or depression. Lastly, hypertension, hypotension and vaso-vagal syncope (VVS) are common in epilepsy patients.

Epileptic seizures are associated with autonomic neuronal dysfunction that result in a broad array of abnormalities of cardiac and pulmonary function. Different pathopsysiological events may contribute to SUDEP in different patients, and the mechanism is probably multifactorial. Without intervention, respiratory events, including airway obstruction, central apnea and neurogenic pulmonary edema are probably terminal events. In addition, cardiac arrhythmia and anomalies, during the ictal and interictal periods, leading to arrest and acute cardiac failure also plays an important role in potentially terminal events. For example, the paper "Electrocardiographic Changes at Seizure Onset", Leutmezer, et al., Epilepsia 44(3): 348-354, 203 describes cardiovascular anomalies, such as heart rate variability (HRV), tachycardia and bradycardia, that may precede, occur simultaneous or lag behind EEG seizure onset. "Cardiac Asystole in Epilepsy: Clinical and Neurophysiologic Features", Rocamora, et al., Epilepsia 44(2): 179-185, 2003 reports that cardiac asystole is "provoked" by the seizure. "Electrocardiograph QT Lengthening Associated with Epileptiform EEG Discharges—a Role in Sudden Unexplained Death in Epilepsy", Tavemor, et al., Seizure 5(1): 79-83, March 1996 reports QT lengthening during seizures in SUDEP patients versus control. "Effects of Seizures on Autonomic and Cardiovascular Function", Devinsky Epilepsy Currents 4(2): 43-46, March/April 2004 describes ST segment depression and T-wave inversion, AVB, VPC and BBB during or immediately after a seizure. "Sudden Unexplained Death in Children with Epilepsy", Donner, et al., Neurology 57: 430-434, 2001 reports that bradycardia is frequently preceded by hypoventilation or apnea suggesting that heart rate changes during seizures may be a result of cardiorespiratory reflexes. Lastly, "EEG and ECG in Sudden Unexplained Death in Epilepsy", Nei, et al., Epilepsia 45(4) 338-345, 2004 reports on sinus tachycardia during or after seizures.

Patients with a psychiatric illness, such as major depressive disorder (MMD), are also at higher risk for developing cardiac problems. A strong link between depression and cardiac death has been established. Some have postulated cardiac vagal control (CVC) is impaired in patients with depression. Others have shown major depression is associated with reduced baroreflex sensitivity (BRS), a predisposing factor for sudden cardiac death. Anxiety, which is central to OCD, has also been shown to be related with a reduction in baroreflex receptor activity. Thus, evidence suggests autonomic function is altered in depression patients, with decreased vagal activity and/or increased sympathetic arousal as possible explanations for the observed cardiac problems.

Treatment therapies for epilepsy, psychiatric illness, and other nervous system disorders can include any number of possible modalities alone or in combination including, for example, electrical stimulation, magnetic stimulation, drug infusion, and/or brain temperature control. Each of these treatment modalities can be operated using an open loop scheme, where therapy is continuously or intermittently delivered based on preprogrammed schedule. Alternatively, a closed-loop scheme may be used, in which the therapy is delivered to the patient based on information coming from a sensed signal.

An exemplary closed-loop feedback control technique includes receiving from a monitoring element a neurological signal that carries information about a symptom, a condition, or a nervous system disorder. The neurological signal can include, for example, electrical signals (such as EEG, EcoG, and/or EKG), chemical signals, other biological signals (such as change in quantity or neurotransmitters), temperature signals, pressure signals (such as blood pressure, intracranial pressure or cardiac pressure), respiration signals, heart rate signals, pH-level signals, and peripheral nerve signals (cuff electrodes on a peripheral nerve). Monitoring elements include, for example, recording electrodes or various types of sensors.

Standard diagnostic EEG sensing requires two electrodes in contact with body tissue. The first electrode is placed near the desired source of the electrical activity that the physician desires to monitor, and is referred to as active. The second electrode, referred to as the reference, is typically placed outside of the cranium away from the desired source of electrical activity. For example, the reference electrode may be attached to the ear or mastoid, or at the back of the head. Such locations are considered "inactive" since sensing from these areas produces a potential that is close to zero. In a monitoring system or device, differential amplifiers measure the voltage difference between the reference electrode and other active electrodes located within the brain. The resulting intracranial signals are amplified and displayed as channels of EEG activity.

For implantable devices that perform EEG sensing, it is desirable to have the reference electrode contained within the body. If the signals are to be used for seizure detection, it is desirable that the reference electrode be remote from the seizure focus. The active electrodes are positioned either in direct or indirect contact with brain structures affecting a neurological condition for which sensing is being performed. For example, to treat epilepsy the active electrodes may be implanted in brain tissue at or near the seizure focus where they can sense EEG signals, detect a seizure event, and provide stimulation therapy. Conversely, the active electrodes may be positioned in an anatomical target distant from the seizure focus, but which is connected to the seizure focus by way of neuronal pathway projections. Activating pathway projections with electrical stimulation from a distant site (i.e., thalamus) may influence seizure activity at the focus (i.e., hippocampus/amygdala). Similarly, to treat a psychiatric illness such as major depressive disorder or OCD, the active electrodes may be implanted directly in brain tissue involved in mood regulation for depression or OCD, such as the internal capsule or subgenual cingulate cortex (Area 25). Alternatively, the active electrodes may be positioned at distant sites within the limbic-cortical circuit, which have connections to these mood regulating regions of the brain. With either approach, it is desirable to have a single electrode positioned away from the active electrodes, which can function as a reference for EEG sensing and/or function as an indifferent electrode for monopolar stimulation.

For patients being treated for a neurological condition, it is desirable to further refine the monitoring and treatment of neurological events, and when appropriate, provide treatment for co-morbid cardiac detected events. To achieve this, what is desired is a neurostimulation device that treats neurological conditions while monitoring the patient's cardiac state, with provisions to enable cardiac therapy if deemed necessary.

In addition, for some patients it would be beneficial to be able to regulate the cardiac therapy using brain state information, particularly in cases where the change in cardiac state is part of the neurological event. For example, some changes in heart rate function during a neurological event, such as a seizure or panic attack (i.e., tachy episodes, brief asystolic pauses, etc.) are considered normal—the body's reaction to dealing with the event—and do not necessitate cardiac treatment. Inadvertent pacemaker activation during such episodes may interfere with physiological processes aimed at terminating them. Thus, means to regulate the cardiac therapy during seizures and other neurological states would be beneficial.

Currently, there are no neurological devices that perform these functions.

SUMMARY

The embodiments of the present invention describe a neurostimulation device that treats both a patient's neurological disorder and co-morbid cardiac events. The implantable medical device such as an implantable pulse generator (IPG) incorporates EEG sensing for monitoring and treating neurological conditions, and leadless ECG sensing for monitoring cardiac signals. The system has three leads on the IPG housing for monitoring the ECG signals, two of which are required for actual cardiac measurements. The best two are determined via visual inspection of signals in a programmer. Position of the IPG relative to the heart determines which pair may work best. Instead of discarding the unused electrode (the one not used for ECG measurements), as is typically done, it is used as a remote reference electrode for monitoring brain (EEG) signals.

The implantable device also has a connector block with provisions for cardiac leads, which may be used/enabled when needed. If significant co-morbid cardiac events are observed in the patient (via leadless ECG monitoring), then cardiac leads may be subsequently connected for therapeutic use. In one embodiment, cardiac monitoring is performed via the leadless ECG electrodes, and cardiac therapy is delivered via the cardiac leads. In another embodiment, leadless sensing is switched to direct sensing once cardiac therapy connections are made (with allowance for monopolar stimulation to the brain and/or heart).

DETAILED DESCRIPTION

The following detailed description is merely exemplary in nature and is not intended to limit the embodiments of the invention or the application and uses of the embodiments of the invention. Furthermore, there is no intention to be bound by any expressed or implied theory presented in the preceding technical field, background, brief summary or the following detailed description.

Figure 1:
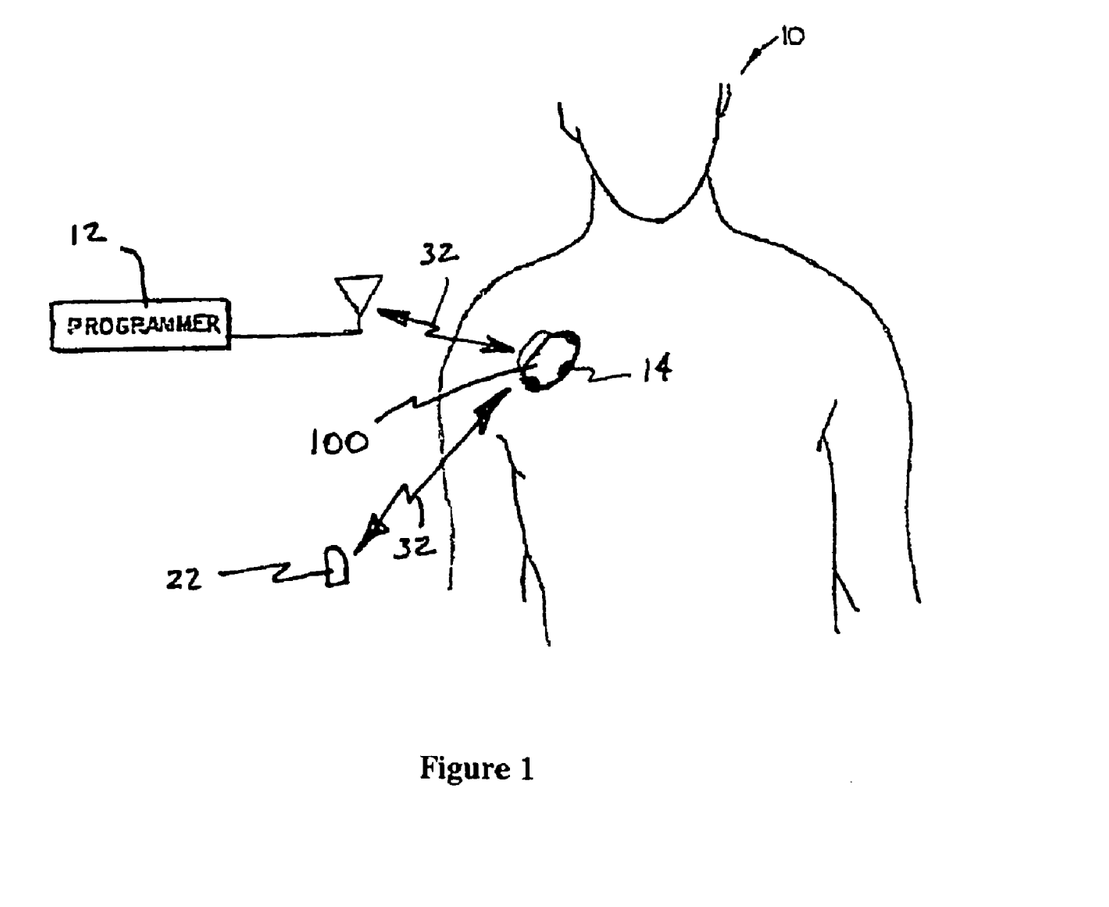
FIG. 1 is a simplified schematic view of a thoracic cavity leadless medical device implanted in a patient that can monitor cardiac and neurological parameters.

FIG. 1 is a simplified schematic view of one embodiment of an implantable medical device 100 implanted in a patient 10 according to an embodiment of the invention. The device 100 is meant to be implanted in a patient and, in one embodiment, the device 100 is a pacemaker, and in another, it is a defibrillator. In accordance with conventional practice in the art, the device 100 has a hermetically sealed, biologically inert outer casing, which itself may be conductive so as to serve as an indifferent electrode in the pacemaker's pacing/sensing circuit. A programmer 12 is used to program the medical device as is well known. The programmer 12 communicates with the medical device 100 via a 2-way telemetry link 32. In addition, the medical device 100 stores diagnostic data which can be uplinked and evaluated by the patient's physician utilizing programmer 12 via the 2-way telemetry link 32. An external patient activator 22 may optionally allow the patient 10, or other care provider (not shown), to manually activate the recording of diagnostic data.

Figure 2:
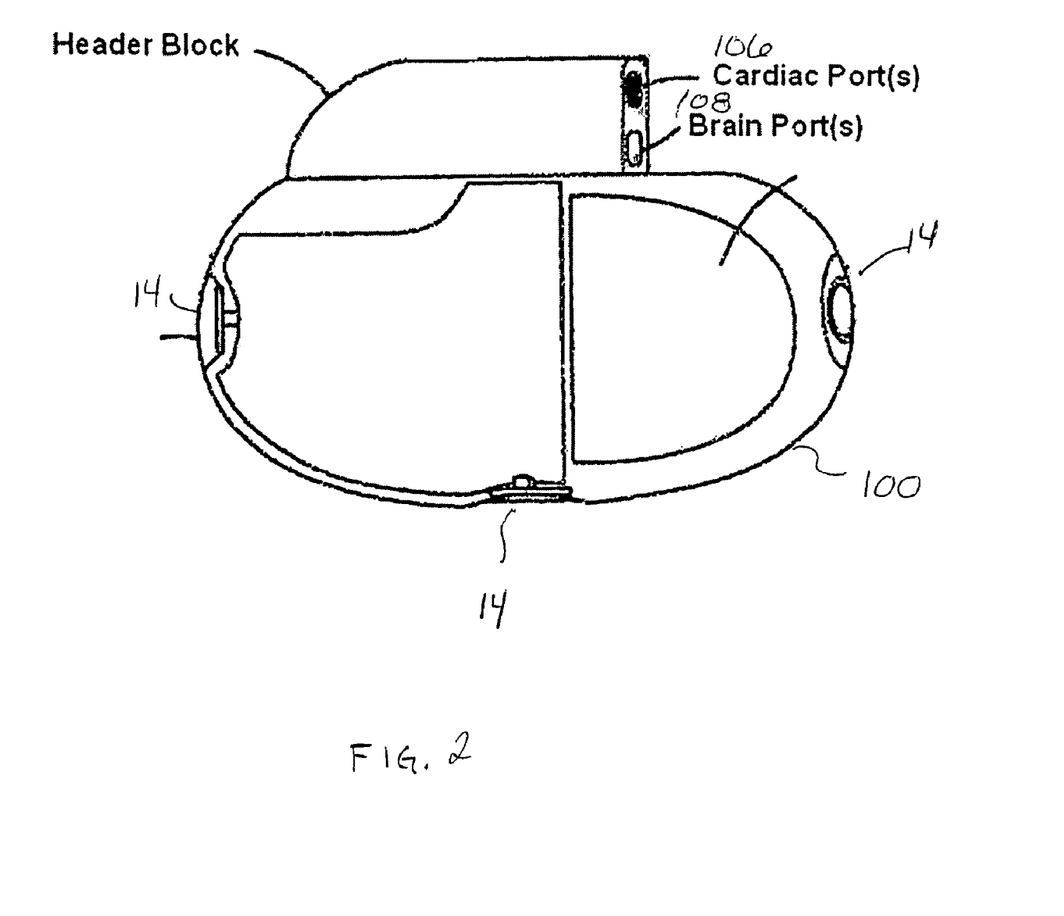
FIG. 2 is a simplified schematic of an implantable medical device shown in FIG. 1 according to an embodiment of the invention.

FIG. 2 is a simplified schematic of an implantable medical device 100 according to an embodiment of the invention. The device 100 has a header block 102 that houses two ports, a cardiac port 106 and a brain port 108. The cardiac port 106 may be used with cardiac leads (not shown) that can be electrically coupled to the device in the cardiac port. The cardiac leads, as will be discussed hereinafter, may extend into or near a patient's heart as is well known to those of ordinary skill in the art.

The brain port 108 may be used with cranial or brain leads (not shown) that can be electrically coupled to the device through the brain port 108. The brain leads, as will be described hereinafter, may extend into or near a patient's brain as is well known to those of ordinary skill in the art.

Device 100, as stated above, typically includes one or more monitoring elements 14 such as several subcutaneous spiral electrodes that are embedded individually into three or four recessed casings placed in a complaint surround that is attached to the perimeter of implanted monitor 100 as substantially described in U.S. Pat. Nos. 6,512,940 "Subcutaneous Spiral Electrode for Sensing Electrical Signals of the Heart" to Brabec, et al. and 6,522,915 "Surround Shroud Connector and Electrode Housings for a Subcutaneous Electrode Array and Leadless ECGS" to Ceballos, et al. which are incorporated herein by reference. These electrodes 14, which will be referred to as leadless electrodes, are electrically coupled to circuitry of the implanted Device 100 to allow the detection of cardiac depolarization waveforms (as substantially described in U.S. Pat. No. 6,505,067 "System and Method for Deriving a Virtual ECG or EMG Signal" to Lee, et al.) that may be further processed to detect cardiac electrical characteristics (e.g., heart rate, heart rate variability, arrhythmias, cardiac arrest, sinus arrest and sinus tachycardia). Further processing of the cardiac signal amplitudes may be used to detect respiration characteristics (e.g., respiration rate, minute ventilation, and apnea). In addition, one or more of the leadless electrodes may be used as an EEG reference electrode for sensing neurological events as will be described hereinafter. Use of the device will be described in detail with reference to the flow chart of FIG. 6.

The device 100 may be used as a full monitor where the term "full monitor" is used to describe a monitor that is capable of monitoring the brain (such as by monitoring a brain signal such as an electroencephalogram (EEG)) and additionally the heart or pulmonary system or both. This will allow the device to collect neurological signals and cardio-vascular signals. Monitoring of more than one physiological signal allows for greater understanding of the total physiological condition of the patient. For example, prolonged or generalized seizures put patients at higher risk for SUDEP, the EEG monitoring may be programmed to provide alerts when a neurological event has exceeded a predetermined duration or severity.

Figure 3:
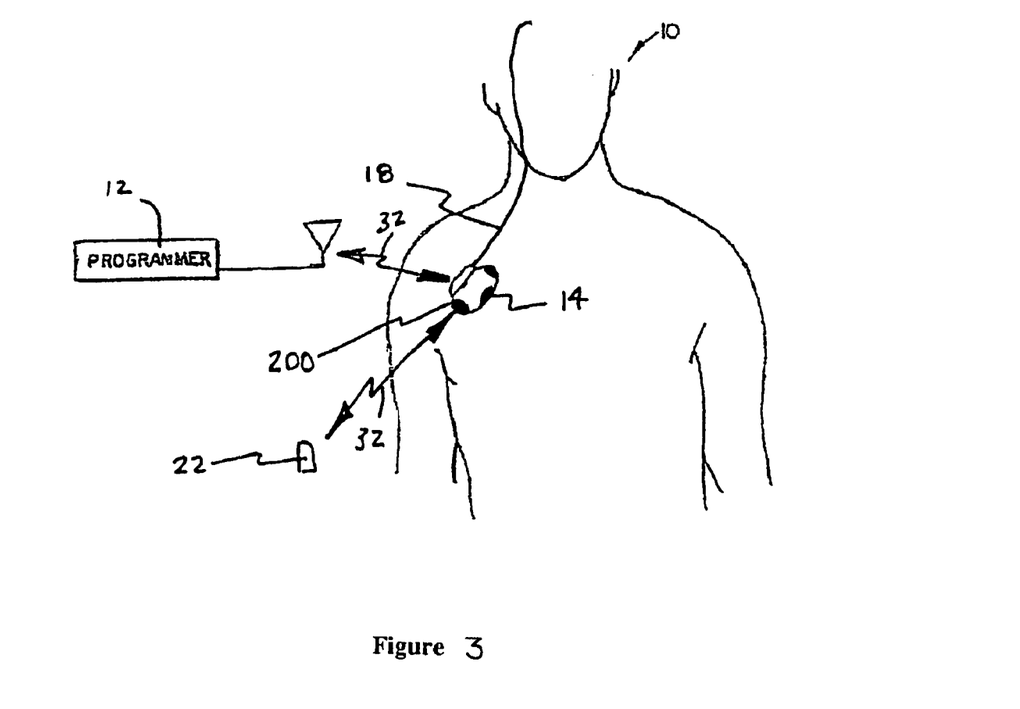
FIG. 3 is a simplified schematic view of an alternative embodiment thoracic leadless and cranial leaded medical device implanted in a patient that monitors cardiac and neurological parameters.

FIG. 3 is a simplified schematic view of a full monitor device 200 implanted in a patient 10. Device 200 continuously senses and monitors cardiac and brain function of patient 10 via one or more brain monitoring elements 18 and one or more cardiac monitoring elements 14. Brain monitoring elements 18 may be for example, one or more brain leads each having one or more electrodes. Such a brain lead may be any lead capable of sensing brain activity such as EEG. For example, brain monitoring element 18 may be a deep brain lead, a cortical lead or an electrode placed on the head externally. Cardiac monitoring elements 14 may be cardiac leads or other types of sensors or electrodes capable of picking up cardiac signals. These monitoring elements allow detection of cardiac and neurological events and the recording of data and signals pre and post event. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data.

The term "brain monitoring element" used herein means any device, component or sensor that receives a physiologic signal from the brain or head of a patient and outputs a brain signal that is based upon the sensed physiologic signal. Some examples of a brain monitoring element include leads, electrodes, chemical sensors, biological sensors, pressure sensors, and temperature sensors. A monitoring element does not have to be located in the brain to be a brain monitoring element. The term brain monitoring element is not the same so the term "monitor" also used herein, although a brain monitoring element could be part of a monitor.

The term "cardiac monitoring element" used herein means any device, component or sensor that receives or infers a physiological signal from the heart of a patent and outputs a cardiac signal that is based upon sensed physiological signal. Some examples of cardiac monitoring elements include leads, electrodes, chemical sensors, biological sensor, pressure sensors and temperature sensors. A monitoring element does not have to be located in the heart or adjacent to the heart to be a cardiac monitoring element. For example, a sensor or electrode adapted for sending a cardiac signal and placed on the housing of an implantable device is a cardiac monitoring element. Furthermore, a cardiac monitoring element could be an externally placed sensor such as a Holter monitoring system. The term "cardiac monitoring element" is not the same as the term "monitor" also used herein although a cardiac monitoring element could be a part of a monitor.

Figure 4:
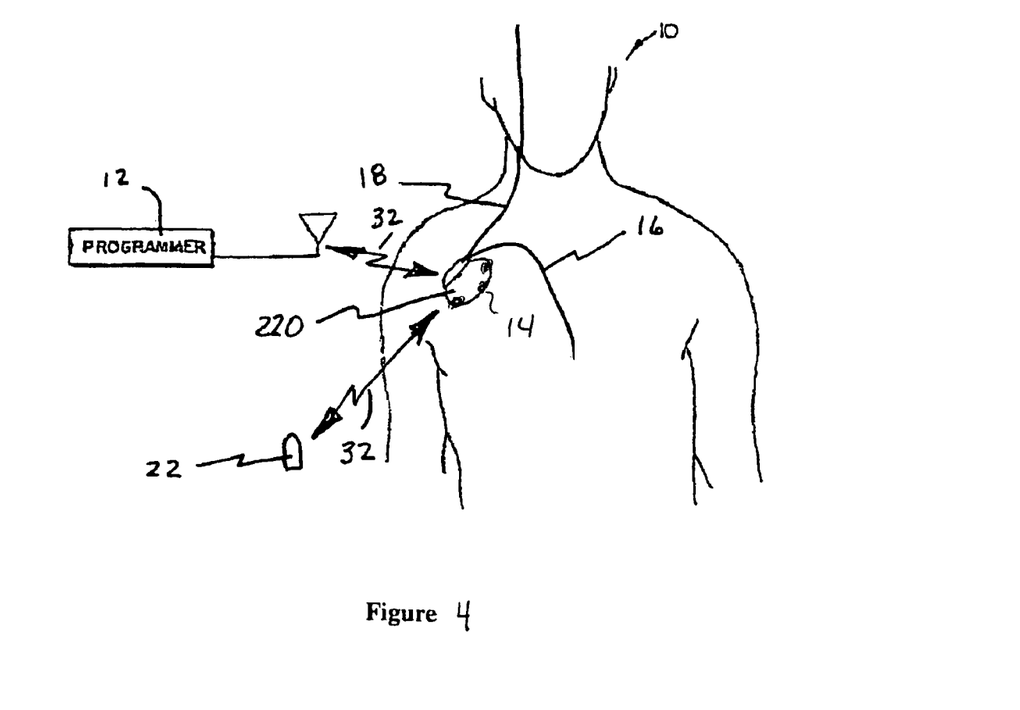
FIG. 4 is a simplified schematic view of an alternative embodiment cardiac and cranial leaded medical device implanted in a patient that monitors cardiac and neurological parameters.

FIG. 4 is a simplified schematic view of a second embodiment of a full Monitor 220 implanted in a patient 10. Monitor 220 continuously senses and monitors cardiac and brain function of patient 10 via cardiac lead(s) 16 and a brain lead 18 to allow detection of cardiac and neurological events and the recording of data and signals pre and post event. Disposed generally near the distal end of each lead 16 and 18 are one or more exposed conductive electrodes for receiving electrical cardiac and neurological signals and/or for delivering electrical pacing stimuli to the heart and/or stimulation to the brain. As will be appreciated by those of ordinary skill in the art, leads may be implanted with its distal end situated in the atrium and/or ventricle of the heart, for example. Stored diagnostic data is uplinked and evaluated by the patient's physician utilizing programmer 12 via a 2-way telemetry link 32. An external patient activator 22 may optionally allow the patient 10, or other care provider (not shown), to manually activate the recording of diagnostic data.

Figure 5:
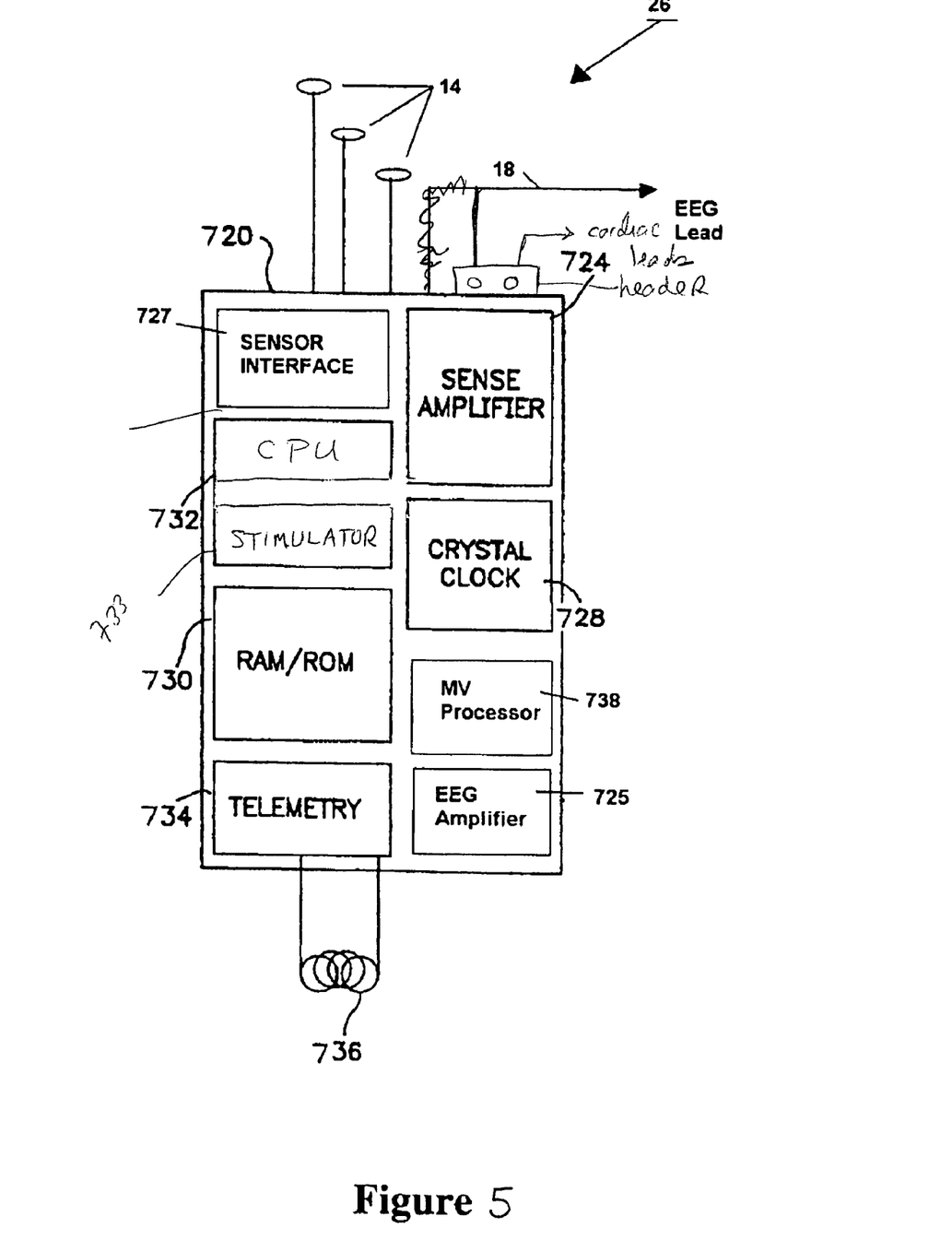
FIG. 5 is a simplified block diagram of an implantable medical device shown in FIGS. 1-4.

FIG. 5 is a simplified block diagram of the electronic circuitry that makes up the implantable medical device. As can be seen from FIG. 5 the device comprises a primary control circuit 720. Much of the circuit associated with the primary control circuit is of conventional design, in accordance, for example, with what is disclosed in U.S. Pat. No. 5,052,388 to Sivula et al. entitled "Method and Apparatus for Implementing Activity Sensing in a Pulse Generator." To the extent that certain components of the device are conventional in their design and operation, such components will not be described herein in detail, as it is believed that design and implementation of such components would be a matter of routine to those of ordinary skill in the art. For example, primary control circuit includes sense amplifier circuitry 724, a crystal clock 728, a random-access memory and a read-only memory (RAM/ROM) unit 730, a central processing unit (CPU) 732, a MV processor circuit 738 and a telemetry circuit 734, all of which are well-known in the art.

Device 100 preferably includes internal telemetry circuit 734 so that it is capable of being programmed by means of external programmer/control unit 12 via a 2-way telemetry link 32 (shown in FIG. 1). Programmers and telemetry systems suitable for use in the practice of the present invention have been well known for many years. Known programmers typically communicate with an implanted device via a bi-directional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Models 9790 and CareLink® programmers, commercially available from Medtronic, Inc., Minneapolis, Minn. Various telemetry systems for providing the necessary communications channels between an external programming unit and an implanted device have been developed and are well known in the art. Telemetry systems believed to be suitable for the purposes of practicing the present invention are disclosed, for example, in the following U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modeled as an air-core coupled transformer. An example of such a telemetry system is shown in the above-referenced Thompson et al. '063 patent.

In order to communicate digital data using RF telemetry, a digital encoding scheme such as is described in the above-reference Wyborny et al. '404 patent can be used. In particular, for downlink telemetry a pulse interval modulation scheme may be employed, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encode a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

As depicted in FIG. 1 programming units such as the above-referenced Medtronic Models 9790 and CareLink® programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

As previously noted, primary control circuit 720 includes central processing unit 732 which may be an off-the-shelf programmable microprocessor or microcontroller, but in the presently preferred embodiment of the invention is a custom integrated circuit. Although specific connections between CPU 732 and other components of primary control circuit 720 are not shown in FIG. 5, it will be apparent to those of ordinary skill in the art that CPU 732 functions to control the timed operation of sense amplifier circuit 724 under control of programming stored in RAM/ROM unit 730. It is believed that those of ordinary skill in the art will be familiar with such an operative arrangement.

With continued reference to FIG. 5, crystal oscillator circuit 728, in the presently preferred embodiment a 32,768-Hz crystal controlled oscillator, provides main timing clock signals to primary control circuit 720.

It is to be understood that the various components of monitor 100 depicted in FIG. 5 are powered by means of a battery (not shown), which is contained within the hermetic enclosure of monitor 100, in accordance with common practice in the art. For the sake of clarity in the figures, the battery and the connections between it and the other components of monitor 100 are not shown.

With continued reference to FIG. 5, sense amplifier 724 is coupled to monitoring elements 14 such as subcutaneous electrodes. Cardiac intrinsic signals are sensed by sense amplifier 724 as substantially described in U.S. Pat. No. 6,505,067 "System and Method for Deriving a Virtual ECG or EGM Signal" to Lee, et al. Further processing by CPU 732 allows the detection of cardiac electrical characteristics/anomalies (e.g., heart rate, heart rate variability, arrhythmias, cardiac arrest, sinus arrest and sinus tachycardia) that would be a matter of routine to those of ordinary skill in the art.

Upon detection of either a cardiac or respiration anomaly, CPU 732, under control of computer executable instruction in firmware resident in RAM/ROM 730, will initiate recording of the appropriate diagnostic information into RAM of RAM/ROM 730, initiate a warning or alert to the patient, patient caregiver, or remote monitoring location.

With continued reference to FIG. 5, device 100 may be coupled to cardiac leads 16 through the cardiac port in the header which, when implanted, extend transvenously between the implant site of Monitor 120 and the patient's heart (not shown). For the sake of clarity, the connections between leads 16 and the various components of Monitor 720 are not shown in FIG. 5, although it will be clear to those of ordinary skill in the art that, for example, leads 16 will necessarily be coupled, either directly or indirectly, to sense amplifier circuitry 724 in accordance with common practice, such that cardiac electrical signals may be conveyed to sensing circuitry 724, via leads 16. Cardiac leads 16 may consist of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

Sensed cardiac events are evaluated by CPU 732 and software stored in RAM/ROM unit 730. Cardiac anomalies detected include heart rate variability, QT variability, QT, sinus arrest, syncope, ST segment elevation and various arrhythmias such as sinus, atrial and ventricular tachycardias.

Heart rate variability may be measured by the method and apparatus as described in U.S. Pat. No. 5,749,900 "Implantable Medical Device Responsive to Heart Rate Variability Analysis" to Schroeppel, et al. and U.S. Pat. No. 6,035,233 "Implantable Medical Device Responsive to Heart Rate Variability Analysis" to Schroeppel, et al. Schroeppel '900 and '233 patents describe an implantable cardiac device that computes time intervals occurring between successive heartbeats and then derive a measurement of heart rate variability from epoch data for predetermined time periods. The Schroeppel device then compares measurement of heart rate variability with previously stored heart rate variability zones, which define normal and abnormal heart rate variability.

QT variability may be measured by the method and apparatus as described in U.S. Pat. No. 5,560,368 "Methodology for Automated QT Variability Measurement" to Berger. The Berger '368 patent utilizes a "stretchable" QT interval template started at the beginning of the QRS complex and terminating on the T-wave to determine beat-to-beat variability.

QT may be measured by the method and apparatus as described in U.S. Pat. No. 6,721,599 "Pacemaker with Sudden Rate prop Detection Based on QT Variations" to deVries. The de Vries '599 patent measures QT interval real time and compares the instantaneous value to a calculated mean via a preprogrammed threshold change value.

Syncope may be detected by the methods and apparatus as described in U.S. Pat. No. 6,721,599 "Pacemaker with Sudden Rate prop Detection Based on QT Variations" to deVries. The de Vries '599 patent utilizes a sudden rate change and a real time QT interval measurement compared to a QT mean to detect sudden rate drop and neurally mediated syncope.

ST segment elevation (an indicator of myocardial ischemia) may be detected by the methods and apparatus as described in U.S. Pat. No. 6,128,526 "Method for Ischemia Detection and Apparatus for Using Same" to Stadler, et al. and U.S. Pat. No. 6,115,630 "Determination of Orientation of Electrocardiogram Signal in Implantable Medical devices" to Stadler, et al. The Stadler '526 and '630 patents describe a system that compares a sampled data point prior to an R-wave complex peak amplitude to multiple samples post R-wave event to detect ST segment elevation.

Arrhythmias such as sinus, atrial and ventricular tachycardias may be detected by the methods and apparatus as described in U.S. Pat. No. 5,545,186 "Prioritized Rule Based Method and Apparatus for Diagnosis and Treatment of Arrhythmias" to Olson, et al.

Sinus arrest may be detected by the methods and apparatus as described above in the Olson '186 patent.

In the presently disclosed embodiment, two leads are employed—an atrial lead having atrial TIP and RING electrodes, and a ventricular lead having ventricular TIP and RING electrodes. In addition, as noted above, the conductive hermetic canister of Monitor 120 serves as an indifferent electrode.

As previously noted, primary control circuit 720 includes central processing unit 732 which may be an off-the-shelf programmable microprocessor or microcontroller, but in the presently preferred embodiment of the invention is a custom integrated circuit. Although specific connections between CPU 732 and other components of primary control circuit 720 are not shown in FIG. 5, it will be apparent to those of ordinary skill in the art that CPU 732 functions to control the timed operation of sense amplifier circuit 724 under control of programming stored in RAM/ROM unit 730. It is believed that those of ordinary skill in the art will be familiar with such an operative arrangement.

With continued reference to FIG. 5, crystal oscillator circuit 728, in the presently preferred embodiment a 32,768-Hz crystal controlled oscillator, provides main timing clock signals to primary control circuit 720 and to minute ventilation circuit 738.

It is to be understood that the various components of Monitor 720 depicted in FIG. 5 are powered by means of a battery (not shown), which is contained within the hermetic enclosure of Monitor 720, in accordance with common practice in the art. For the sake of clarity in the figures, the battery and the connections between it and the other components of Monitor 720 are not shown.

In addition the primary control circuit 720 of FIG. 5 also includes an EEG amplifier 725 to amplify and sense EEG signals from a cranially implanted lead 18 or, alternatively, device mounted electrodes 14. A stimulator 733 is included to provide electrical stimulation to the brain if desired. Cranial or brain lead 18 is coupled to the primary control circuit through the brain port in the header ECG sensing in the cranium may be accomplished by leadless ECG sensing as described in the above Brabec '940, Ceballos '915 and Lee '067 referenced patents. Alternatively, cardiac rate and asystole may be inferred from a dP/dt signal described above in the Anderson '813 patent; an acoustic signal described above in the Kieval '177 patent; an $O_2$ sat signal described above in Moore '701 patent; a dT/dt signal described above in the Weijand '244 patent; a flow signal described above in the Olson '009; a strain gauge signal described above in the Bowman '759 patent; and a blood parameter sensor (such as oxygen, pulse or flow) located on a V-shaped lead described in the Taepke '318 patent.

The CPU 732, in conjunction with a software program resident in RAM/ROM 730, integrates the information from the sensed cardiac and EEG signals, detects the onset of cerebral, cardiac anomalies, formats and stores diagnostic data for later retrieval by the patient's clinician and, optionally, may warn or alert the patient, patient caregiver or remote monitoring location.

Figure 6:
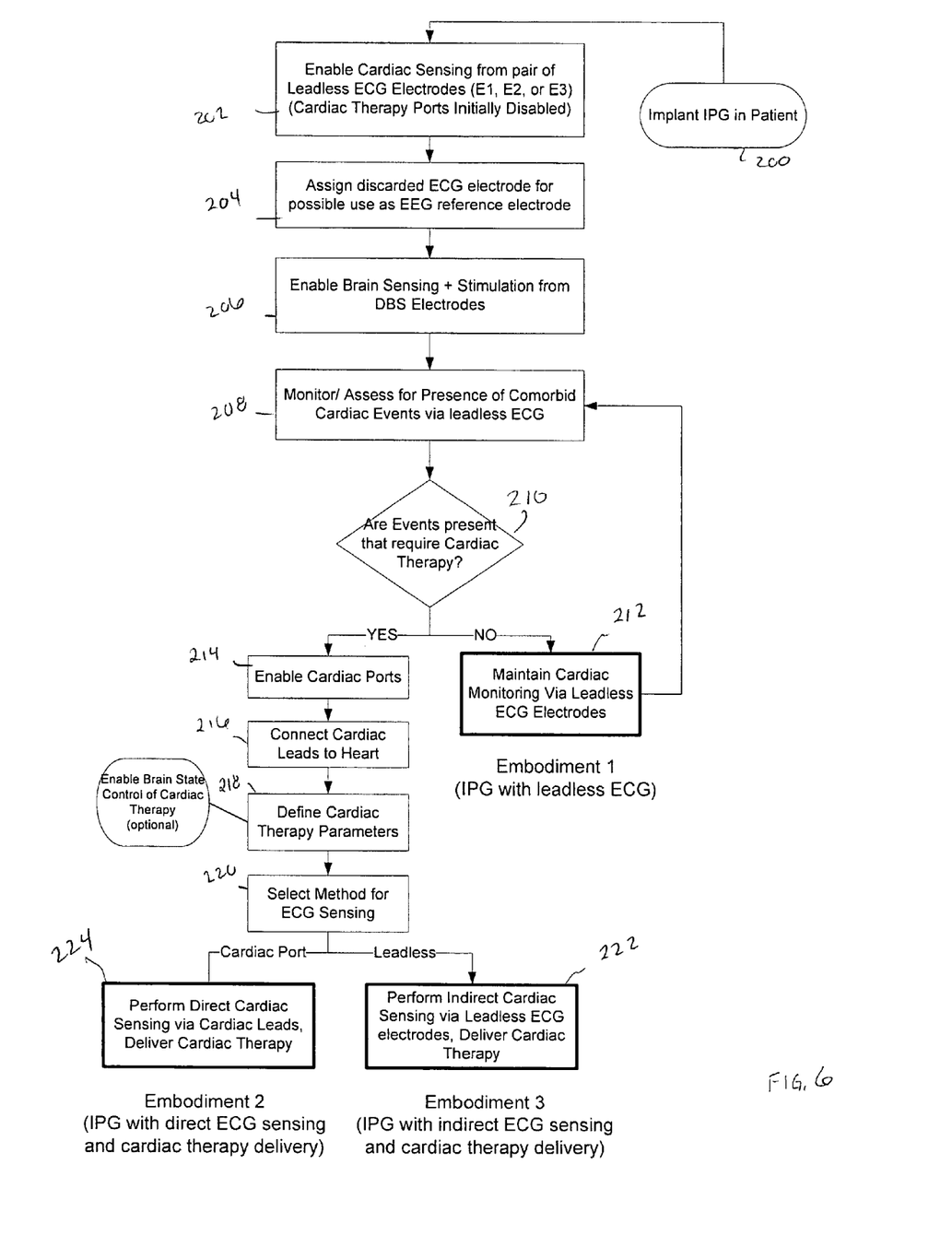
FIG. 6 is a flowchart of a method according to an embodiment of the invention.

FIG. 6 is a flow chart illustrating the use of the device. At block 200, the device is implanted in a patient. At block 202 cardiac sensing is enabled from two of the leadless electrodes. The cardiac port in the header is electrically disabled. This may be done before or after the device is implanted in a patient. Because the device is implanted without cardiac leads, a cardiologist is not required to perform the surgery. At block 204, the leadless electrode not used for cardiac sensing may be used as an EEG reference electrode as will be discussed hereinafter. At block 206, if the brain port is enabled, and the device 100 is to be implanted with a brain lead, the brain sensing and stimulation circuitry is enabled. The leadless electrode not being used for cardiac sensing may be used as a reference EEG electrode. If the device is to be implanted without a brain lead then the step at block 206 may be omitted or performed at some subsequent time.

At block 208, the cardiac events sensed by the pair of leadless electrodes are monitored and/or assessed for the presence of co-morbid cardiac events, in one embodiment. At block 210 it is determined whether the cardiac events monitored/assessed require cardiac therapy. If it is determined that the monitored/assessed cardiac events do not require cardiac therapy, then at block 212 cardiac monitoring via the leadless electrodes is continued.

If it is determined at block 210 that the cardiac event(s) monitored/assessed do require cardiac therapy, then at block 214 the cardiac port in the header is enabled. At block 216 cardiac leads are coupled to the enabled cardiac port and the distal ends of the leads are placed in or near the patient's heart. It will be recognized that at block 216, the patient will have to undergo additional surgical procedure to add the cardiac leads This will now require the services of a cardiologist whereas the initial implantation of the device 100 did not. Thus, with the method and system of the device according to the embodiments of the invention, the services of a cardiologist are not needed until it is determined that cardiac events exist that require cardiac therapy.

At block 218, cardiac therapy parameters are defined as is well known to those of ordinary skill in the art. In addition, brain state control of cardiac therapy, as described in copending application filed concurrently herewith entitled "System and Method for Utilizing Brain State Information to Modulate Cardiac Therapy" which is incorporated herein by reference, may be enabled.

At block 220 one of two methods of ECG sensing are selected. One method involves indirect cardiac sensing via the leadless electrodes as defined at block 222. The other involves direct cardiac sensing with the cardiac leads as defined at block 224. In either case, cardiac therapy is delivered using the cardiac lead(s).

As previously described, in another embodiment of the invention, a brain lead may be coupled to the brain port of the header. The brain lead typically will have electrodes at its opposite end which are implanted in or near a patient's brain. This implantation may be done at the time the device is initially implanted or it may be performed subsequently. The leadless electrode that is not in use for sensing cardiac signals may be enabled as an EEG reference electrode.

The processor includes sensing circuitry adapted to receive and process electrical signals received by the electrode(s) at the distal end of the brain lead and the EEG reference electrode. The processor may also include a pulse generator where the electrode(s) at the distal end of the brain lead may receive stimulating pulses from the pulse generator and deliver pulses to tissue in which the electrode(s) is implanted.

The distal end of the brain lead may have at least two electrodes coupled to the pulse generator to deliver bipolar stimulation to the tissue as is well known to those of ordinary skill in the art. Alternatively, the leadless electrode may be used as an indifferent electrode and the electrode located at the distal end of the brain lead may be used to deliver monopolar stimulation to the tissue. Thus the leadless electrode not used for cardiac sensing may act as an indifferent electrode for monopolar stimulation and/or as a reference electrode for sensing electrical activity.

Electrical impulses occur as current flows between an active electrode and an indifferent electrode through the body tissue. FIG. 3 is a deep brain EEG sensing and stimulation system.

In a preferred embodiment, an implantable pulse generator (IPG) 10 is implanted proximate to the patient's clavicle. The IPG 10 includes a pulse generating source that is coupled to, and in some cases controlled by, EEG sensing circuitry. A lead extension 20 has a proximal end that is coupled to the pulse generating source in the IPG 10, and a distal end that is coupled to an extension connector 22, which is typically implanted near the patient's cranium. The extension connector 22 connects the lead extension 20 to an intracranial lead 23 in a manner that enables a physician to detach the intracranial lead 23 from the lead extension 20, and thereby remove or adjust the IPG 10 without disrupting the intracranial lead position about the patient's brain. One or more deep brain stimulation electrodes 28 are positioned near the intracranial lead distal end 26, and are inserted into targeted brain tissue. The lead extension 20, connector 22, and lead 23 usually extend from the IPG 10 between the dermis and the cranium. The electrodes 28 are positioned into or near the targeted brain tissue by passing some or all of the intracranial lead distal end 26 through a burr hole 24 surgically bored through the cranium.

In this and other embodiments, the remote electrode 14 is adapted to function in various capacities, including as a reference electrode for sensing electrical signals including EEG signals, and as an indifferent electrode during monopolar stimulation.

It is noted that many embodiments of the invention may reside on any hardware embodiment currently understood or conceived in the future. Many example hardware embodiments are provided in this specification. These examples are not meant to be limiting of the invention.

What is claimed is:
1. A method comprising:
implanting into a patient a medical device having at least three leadless electrodes located on a housing of the medical device, a brain port, and a cardiac port, the medical device having a processor communicatively coupled to the cardiac port, the brain port, and the at least three leadless electrodes, each of the at least three leadless electrodes adapted for cardiac sensing;
implanting into the patient a brain lead having a proximal end coupled to the brain port and a distal end with at least one electrode, and implanting the distal end in the patient at a location to sense electrical signals from the patient's brain;
disabling the cardiac port either before or after implantation of the device;
determining which of the at least three leadless electrodes will be used for cardiac monitoring and which of the at least three leadless electrodes will instead be used for brain signal monitoring;
enabling cardiac monitoring from two of the at least three leadless electrodes based on the determination;
enabling brain signal monitoring from one of the at least three leadless electrodes adapted for cardiac sensing but not enabled for cardiac monitoring based on the determination, the processor including sensing circuitry adapted to receive and process electrical signals received by the distal end of the brain lead and the one of the at least three leadless electrodes enabled for brain signal monitoring;

monitoring for the presence of cardiac events that may require cardiac therapy;

if no cardiac events that may require therapy are identified, maintaining cardiac monitoring using the two leadless electrodes; and if a cardiac event that may require cardiac therapy is identified, enabling the cardiac port.

2. The method of claim 1 further comprising the step of, if a cardiac event that may require cardiac therapy is identified, coupling proximal ends of cardiac leads to the cardiac port and positioning distal ends of the leads in, or in close proximity to, the heart.

3. The method of claim 2 further comprising the step of, if a cardiac event that may require cardiac therapy is identified, disabling cardiac monitoring from the two leadless electrodes and enabling cardiac monitoring from the cardiac leads.

4. The method of claim 2 further comprising a step of, if a cardiac event that may require cardiac therapy is identified, selecting either the cardiac port or the two leadless electrodes for cardiac monitoring.

5. The method of claim 4 wherein if the cardiac port is selected, performing direct cardiac monitoring with the cardiac leads and, if required, delivering cardiac therapy with the cardiac leads.

6. The method of claim 5 further comprising a step of enabling brain state control of the delivered cardiac therapy.

7. The method of claim 4 wherein if the two leadless electrodes are selected, performing indirect cardiac monitoring with the two leadless electrodes and, if required, delivering cardiac therapy with the cardiac leads.

8. The method of claim 4 further comprising a step of defining cardiac therapy parameters before the step of selecting either the cardiac port or the two leadless electrodes for cardiac monitoring.

9. The method of claim 2 further comprising the step of delivering cardiac therapy with the cardiac leads.

10. The method of claim 1 wherein the processor also includes a pulse generator wherein the at least one electrode on the distal end of the brain lead is adapted to receive stimulating pulses from the pulse generator and deliver pulses to tissue in which the at least one electrode is implanted.

11. The method of claim 10 wherein the one of the at least three leadless electrodes not enabled for cardiac monitoring is a remote electrode coupled to the pulse generator.

12. The method of claim 11 wherein the remote electrode is a reference electrode.

13. The method of claim 11 wherein the remote electrode is an indifferent electrode.

14. The method of claim 13 wherein the at least one electrode may deliver monopolar stimulation.

15. The method of claim 10 further comprising a second electrode located at the distal end of the brain lead coupled to the pulse generator wherein the at least one electrode and the second electrode may deliver bipolar stimulation.

16. The method of claim 1, wherein determining which of the at least three leadless electrodes will be used for cardiac monitoring is based on a visual inspection of signals from the at least three leadless electrodes.

17. The method of claim 1, wherein determining which of the at least three leadless electrodes will be used for brain signal monitoring is based on a visual inspection of cardiac signals from the at least three leadless electrodes.

18. A method comprising:

implanting into a patient a medical device having a plurality of cardiac sensing electrodes and a brain port, the medical device having a processor communicatively coupled to the cardiac sensing electrodes and the brain port;

implanting into the patient a brain lead having a proximal end coupled to the brain port and a distal end with at least one electrode, and implanting the distal end in the patient at a location to sense electrical signals from the patient's brain;

dividing the plurality of cardiac sensing electrodes for use between cardiac monitoring and brain monitoring;

enabling cardiac monitoring from two of the plurality of cardiac sensing electrodes based on the division of the plurality of cardiac sensing electrodes;

enabling brain signal monitoring from one of the plurality of cardiac sensing electrodes not enabled for cardiac monitoring based on the division of the plurality of cardiac sensing electrodes, the processor including sensing circuitry adapted to receive and process electrical signals received by the distal end of the brain lead and the one of the plurality of cardiac sensing electrodes enabled for brain signal monitoring; and assessing the cardiac monitoring for the presence of cardiac events that may require cardiac therapy.

19. The method of claim 18, wherein the medical device further comprises a cardiac therapy port communicatively coupled to the processor, and further comprising the steps of disabling the cardiac therapy port either before or after implantation of the device, if no cardiac events that may require therapy are identified, maintain cardiac monitoring using the cardiac sensing port, if a cardiac event that may require cardiac therapy is identified, enabling the cardiac therapy port, and coupling proximal ends of cardiac leads to the cardiac therapy port after assessing the cardiac monitoring and positioning distal ends of the cardiac leads in, or in close proximity to, the patient's heart, and delivering cardiac therapy with the cardiac leads.

20. The method of claim 18 wherein the processor also includes a pulse generator wherein the at least one electrode on the distal end of the brain lead is adapted to receive stimulating pulses from the pulse generator and deliver pulses to the at least one electrode.

21. The method of claim 20 wherein the cardiac sensing electrode enabled for brain signal monitoring is a remote, leadless electrode coupled to the pulse generator.

22. The method of claim 21 wherein the remote electrode is a reference electrode.

23. The method of claim 21 wherein the remote electrode is an indifferent electrode.

24. The method of claim 23 wherein the at least one electrode may deliver monopolar stimulation.

25. The method of claim 20 further comprising a second electrode located at the distal end of the brain lead coupled to the pulse generator wherein the at least one electrode and the second electrode may deliver bipolar stimulation.

26. The method of claim 18, wherein dividing the plurality of cardiac sensing electrodes for use between brain monitoring and cardiac monitoring is based on a visual inspection of signals from the plurality of cardiac sensing electrodes.

27. An apparatus for leadless acquisition of electrocardiographic data comprising:

a hermetically sealed implantable device including at least three leadless electrodes located on a housing of the medical device, a brain port, and a cardiac therapy port wherein each of the at least three leadless electrodes are adapted for cardiac sensing;

a brain lead having a proximal end coupled to the brain port, the brain lead having a distal end with at least one electrode configured to be implanted in a human at a location to sense electrical signals from the human's brain;

a therapy module coupled to the cardiac therapy port for providing therapeutic output to the heart;

a processor in communication with the at least three leadless electrodes, the brain port, and the cardiac port; and a non-transitory computer readable medium in communication with the processor, the computer readable medium comprising executable instructions for causing the processor to perform the following:

enable two of the at least three leadless electrodes for cardiac monitoring based on a post-implantation determination indicating which of the at least three leadless electrodes will be used for cardiac monitoring;

enable brain signal monitoring from one of the at least three leadless electrodes adapted for cardiac monitoring but not enabled for cardiac monitoring;

receive and process electrical signals received by the distal end of the brain lead and the one leadless electrode enabled for brain signal monitoring;

monitor for the presence of cardiac events that may require cardiac therapy, and if no cardiac event that may require cardiac therapy is identified, maintain cardiac monitoring using the two leadless electrodes; and if a cardiac event that may require cardiac therapy is identified, enable the cardiac therapy port so that cardiac leads may subsequently be coupled to the cardiac port.

28. The apparatus of claim 27 further comprising cardiac leads coupled to the cardiac therapy port.

29. The apparatus of claim 27 wherein the computer readable medium further comprises executable instructions for causing the processor to disable cardiac monitoring from the two leadless electrodes and enable cardiac monitoring from the cardiac leads, if a cardiac event that may require cardiac therapy is identified.

30. The apparatus of claim 27 wherein the computer readable medium further comprises executable instructions for causing the processor to select either the cardiac port or the two leadless electrodes for cardiac monitoring, if a cardiac event that may require cardiac therapy is identified.

31. The apparatus of claim 30 wherein the computer readable medium further comprises executable instructions for causing the processor to perform direct cardiac monitoring with the cardiac leads if the cardiac port is selected and, if required, deliver cardiac therapy with the cardiac leads.

32. The apparatus of claim 30 wherein the computer readable medium further comprises executable instructions for causing the processor to perform indirect cardiac monitoring with the two leadless electrodes if the two leadless electrodes are selected, and, if required, deliver cardiac therapy with the cardiac leads.

33. The apparatus of claim 27 wherein the computer readable medium further comprises executable instructions for causing the processor to enable brain state control of the delivered cardiac therapy.

34. The apparatus of claim 27 wherein the processor also includes a pulse generator wherein the at least one electrode on the distal end of the brain lead is adapted to receive stimulating pulses from the pulse generator and deliver pulses to the at least one electrode.

35. The apparatus of claim 34 further comprising a second electrode located at the distal end of the brain lead coupled to the pulse generator wherein the at least one electrode and the second electrode may deliver bipolar stimulation.

36. The apparatus of claim 34 wherein the one of the at least three leadless electrodes enabled for brain signal monitoring is a remote electrode coupled to the pulse generator.

37. The apparatus of claim 36 wherein the remote electrode is a reference electrode.

38. The apparatus of claim 36 wherein the remote electrode is an indifferent electrode.

39. The apparatus of claim 38 wherein the at least one electrode may deliver monopolar stimulation.

40. The apparatus of claim 27, wherein the computer readable medium further comprises executable instructions for causing the processor to receive a command indicating which of the at least three leadless electrodes will be used for cardiac monitoring and to enable the two of the at least three leadless electrodes based on the command.

41. An apparatus for leadless acquisition of electrocardiographic data comprising:

a hermetically sealed implantable device including at least three leadless electrodes located on a housing of the medical device and a brain port;

a brain lead having a proximal end coupled to the brain port, the brain lead having a distal end with at least one electrode configured to be implanted in a human at a location to sense electrical signals from the human's brain;

a processor in communication with the at least three leadless electrodes and the brain port; and a non-transitory computer readable medium in communication with the processor, the computer readable medium comprising executable instructions for causing the processor to perform the following:

enable two of the at least three leadless electrodes for cardiac monitoring based on a post-implantation determination indicating which of the at least three leadless electrodes will be used for cardiac monitoring;

enable brain signal monitoring from one of the at least three leadless electrodes adapted for cardiac monitoring but not enabled for cardiac monitoring;

receive and process electrical signals received by the distal end of the brain lead and the one leadless electrode enabled for brain signal monitoring; and monitor for the presence of cardiac events that may require cardiac therapy.

* * * * *